United States Patent
Kubota

(10) Patent No.: US 11,266,579 B2
(45) Date of Patent: Mar. 8, 2022

(54) OIL-IN-WATER TYPE EMULSION SOLID COSMETIC

(71) Applicant: SHISEIDO COMPANY, LTD., Tokyo (JP)

(72) Inventor: Shun Kubota, Yokohama (JP)

(73) Assignee: SHISEIDO COMPANY, LTD., Tokyo (JP)

(*) Notice: Subject to any disclaimer, the term of this patent is extended or adjusted under 35 U.S.C. 154(b) by 0 days.

(21) Appl. No.: 16/758,020

(22) PCT Filed: Oct. 30, 2018

(86) PCT No.: PCT/JP2018/040210
§ 371 (c)(1),
(2) Date: Apr. 21, 2020

(87) PCT Pub. No.: WO2019/088056
PCT Pub. Date: May 9, 2019

(65) Prior Publication Data
US 2020/0315929 A1    Oct. 8, 2020

(30) Foreign Application Priority Data

Oct. 31, 2017 (JP) .............................. JP2017-210540

(51) Int. Cl.
| | |
|---|---|
| *A61K 8/06* | (2006.01) |
| *A61K 8/02* | (2006.01) |
| *A61K 8/73* | (2006.01) |
| *A61K 8/81* | (2006.01) |
| *A61K 8/92* | (2006.01) |
| *A61Q 1/00* | (2006.01) |
| *A61Q 17/04* | (2006.01) |
| *A61Q 19/00* | (2006.01) |

(52) U.S. Cl.
CPC .............. *A61K 8/062* (2013.01); *A61K 8/022* (2013.01); *A61K 8/73* (2013.01); *A61K 8/8158* (2013.01); *A61K 8/92* (2013.01); *A61Q 1/00* (2013.01); *A61Q 17/04* (2013.01); *A61Q 19/00* (2013.01); *A61K 2800/48* (2013.01); *A61K 2800/596* (2013.01)

(58) Field of Classification Search
None
See application file for complete search history.

(56) References Cited

U.S. PATENT DOCUMENTS 5,928,655 A    7/1999    Avalle

FOREIGN PATENT DOCUMENTS

| FR | 2794997 A | 12/2000 | |
|---|---|---|---|
| JP | 3242137 | 7/1993 | |
| JP | H0717828 A | 1/1995 | |
| JP | 8-245363 | 9/1996 | |
| JP | 3563815 | 9/1996 | |
| JP | H10236919 A | 9/1998 | |
| JP | H 10291914 | 11/1998 | |
| JP | 11-246352 | 9/1999 | |
| JP | 2003-502394 | 1/2003 | |
| JP | 2003-95862 | 4/2003 | |
| JP | 2014162790 A | 9/2014 | |
| JP | 2018-172305 | 11/2018 | |
| KR | 20140078572 A | 6/2014 | |
| WO | WO-0053641 A1 * | 9/2000 | ............... D06P 1/44 |
| WO | WO-0078442 A1 * | 12/2000 | ............. A61Q 19/00 |

OTHER PUBLICATIONS

PCT/JP2018/040210, International Search Report (ISR) and Written Opinion (WO), dated Feb. 5, 2019, 13 pages—English, 11 pages—Japanese.
Fragrance Journal, Oct. 15, 2014 (date of issue), Oct. 2014 issue (vol. 42, No. 10), pp. 61-67, non-official translation (Kawaguchi, Yoriko, "Application of multifunctional taurine-based water-soluble polymer thickener to cosmetic").
EP 18874034.4, Extended European Search Report dated Jul. 1, 2021, 8 pages—English.

* cited by examiner

*Primary Examiner* — Nannette Holloman
(74) *Attorney, Agent, or Firm* — Andrew F. Young; Nolte Lackenbach Siegel

(57) ABSTRACT

An oil-in-water type emulsion solid cosmetic that causes "adhesion" similar to that of a water-in-oil type emulsion solid cosmetic including wax, while having freshness and a moisturizing effect of an oil-in-water type emulsion substance. An oil-in-water type emulsion solid cosmetic contains (A) at least one hydrophilic thickening agent selected from the group consisting of gellan gum, agar, and copolymers including 2-acrylamide-2-methyl propane sulfonic acid, (B) a higher alcohol, (C) a surfactant, (D) water, and (E) an oil component, wherein the ratio between the blending amount of the (A) hydrophilic thickening agent and the total blending amount of the (B) higher alcohol and the (C) surfactant falls within the range of 3:1-1:9.

9 Claims, No Drawings

OIL-IN-WATER TYPE EMULSION SOLID COSMETIC

CROSS REFERENCE TO RELATED APPLICATIONS

This application relates to and claims priority as a § 371 national phase, from PCT/JP2018/040210 filed Oct. 30, 2018, the entire contents of which are incorporated herein by reference, which in turn claims priority from JP 2017-210540 filed Oct. 31, 2017.

FIGURE SELECTED FOR PUBLICATION

None

TECHNICAL FIELD

The present invention relates to an oil-in-water (type) emulsion solid cosmetic. More specifically, the present invention relates to an oil-in-water emulsion solid cosmetic that achieves a picking up property similar to the picking up property of a water-in-oil emulsion containing wax, while maintaining a fresh feeling and a moisturizing effect of an oil-in-water emulsion.

BACKGROUND ART

Conventional solid cosmetics such as foundations are generally prepared as water-in-oil emulsions containing wax or the like in order to retain their forms. Although the water-in-oil emulsion cosmetics are excellent in a form retention or a property of picking up (pick up) or paying off (pay off) with an applicator such as a puff, these cosmetics have poor freshness upon application, are inferior in moisturizing effect or feeling of hydration, and produce heavy texture or stickiness due to the wax.

On the other hand, oil-in-water emulsion cosmetics produce fresh texture and are also excellent in moisturizing effect. An attempt has been made to prepare a semisolid or solid cosmetic by thickening or solidifying an oil-in-water emulsion (Patent Documents 1 and 2).

However, these cosmetics are not satisfactory in terms of picking up with a puff, texture such as spread on the skin, and long-lasting makeup, though having a refreshing feeling unique to the oil-in-water type cosmetics (Patent Document 3, paragraph 0005).

In Patent Document 3, an oil having a surface tension of 25 or less, hydrocarbon wax, propylene glycol and a derivative thereof are used in combination and dispersed in water using a hydrophilic nonionic surfactant, thereby improving picking up with a puff, etc. as a cosmetic in a solid state that can turn into an emulsion state by the application of stress.

However, Patent Document 3 states that wax is essential. None of the cases have achieved a favorable picking up in an oil-in-water emulsion system without wax.

CITATION LIST

Patent Literature

Patent Document 1: JP 3242137 B
Patent Document 2: JP 3563815 B
Patent Document 3: JP H10-291914 A

SUMMARY OF INVENTION

Technical Problem

An object of the present invention is to provide an oil-in-water emulsion solid cosmetic that achieves "picking up" similar to the picking up provided with a water-in-oil emulsion solid cosmetic containing wax, while having the freshness and moisturizing effect of an oil-in-water emulsion.

Solution to Problem

The present inventor has conducted diligent studies to attain the object and consequently completed the present invention by finding that: an oil-in-water emulsion can be solidified by introducing a lamellar liquid crystal structure to an inner phase (oil phase), adding a specific hydrophilic thickener to an outer phase (water phase), and adjusting the mass ratio of these components to within a specific range; and furthermore, the picking up similar to the picking up provided with a water-in-oil emulsion solid cosmetic (containing wax) can be achieved.

Specifically, the present invention provides an oil-in-water emulsion solid cosmetic comprising
(A) at least one hydrophilic thickener selected from the group consisting of a gellan gum, an agar, and a copolymer comprising 2-acrylamido-2-methylpropanesulfonic acid,
(B) a higher alcohol,
(C) a surfactant,
(D) water, and
(E) an oil,
Wherein: a ratio between a content of the hydrophilic thickener contained in the component (A) and a total content of the higher alcohol (B) and the surfactant (C) is within the range of 3:1 to 1:9.

Advantageous Effects of Invention

The oil-in-water emulsion solid cosmetic of the present invention (hereinafter, also simply referred to as the "cosmetic of the present invention") has freshness, a feeling of coolness (refreshing feeling), a moisturizing effect and a feeling of hydration carried by an oil-in-water emulsion and in addition, can achieve a "picking up" of a cosmetic such as a water-in-oil emulsion cosmetic, which has heretofore been difficult to achieve. Also, the cosmetic of the present invention has a non-conventional distinctive feeling by itself and is excellent in texture.

DESCRIPTION OF EMBODIMENTS

The cosmetic of the present invention comprises an oil droplet having a lamellar liquid crystal structure (including an α-gel structure) as an inner phase (oil phase), and contains a specific hydrophilic thickener in an outer phase (water phase), and can thereby be solidified even without a solid oil such as wax. The obtained solid cosmetic is an oil-in-water emulsion yet can probably achieve "picking up" properties similar to the picking up provided with a water-in-oil emulsion solid cosmetic containing wax or the like, because the liquid crystal structure (α-gel structure) collapses and turns into a gel by the application of the cosmetic with stroke on its surface in the lateral (along with the surface) direction using an applicator such as a puff. Hereinafter, each component constituting the cosmetic of the present invention will be described in detail.

(A) Hydrophilic Thickener

The hydrophilic thickener (A) (also referred to as a "component (A)") for use in the cosmetic of the present invention is at least one member selected from the group consisting of a gellan gum, an agar, and a copolymer comprising 2-acrylamido-2-methylpropanesulfonic acid.

The "gellan gum" is a substance that is produced by *Pseudomonas elodea* in a medium mainly containing glucose, and is containing mainly of heteropolysaccharides consisting of glucose, glucuronic acid and rhamnose (glucose:glucuronic acid:rhamnose ratio=2:1:1). The gellan gum according to the present invention preferably has a molecular weight on the order of 670,000 to 920,000. The structure of the gellan gum is, as represented by the following formula, a linear macromolecular polysaccharide structure consisting of a repeat structure with 1-3 linked glucose, 1-4 linked glucuronic acid, 1-4 linked glucose, and 1-4 linked rhamnose.

[Formula 1]

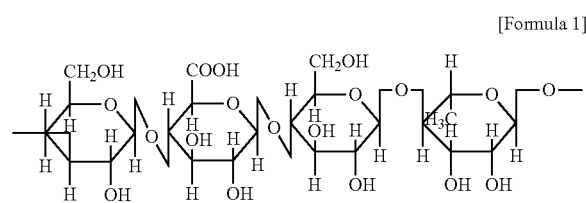

The gellan gum includes deacylated type gellan gum and native type gellan gum, and both of which can be suitably used in the present invention.

The "agar" is not particularly limited as long as the agar is composed mainly of agarose having a high gelling power. The agar may be a natural product or a commercially available product. For example, Ina Agar PS-84, Z-10, AX-30, AX-100, AX-200, T-1, S-5, or M-7 (manufactured by Ina Food Industry Co., Ltd.) can be suitably used as commercially available agar. Alternatively, purified agarose may be used as the agar.

The "copolymer comprising 2-acrylamido-2-methylpropanesulfonic acid" is a copolymer or a crosspolymer comprising 2-acrylamido-2-methylpropanesulfonic acid (AMPS) as a constituent monomer.

Specific examples thereof include N,N-dimethylacrylamide-2-acrylamido-2-methylpropanesulfonic acid (salt) copolymers, acrylamide/2-acrylamido-2-methylpropanesulfonic acid (salt) copolymers, vinylpyrrolidone/2-acrylamido-2-methylpropanesulfonic acid (salt) copolymers, sodium acrylate/2-acrylamido-2-methylpropanesulfonic acid (salt) copolymers, and hydroxyethyl acrylate/2-acrylamido-2-methylpropanesulfonic acid (salt) copolymers. An inorganic salt such as sodium or potassium, or an organic salt such as ammonium is suitable as the "salt" described above. Among others, a cross-linked type N,N-dimethylacrylamide-2-acrylamido-2-methylpropanesulfonic acid (salt) copolymer (crosspolymer) is preferably used. Examples of a commercially available product include "SU-Polymer G-1" (manufactured by TOHO Chemical Industry Co., Ltd.).

The hydrophilic thickener (component (A)) according to the present invention is one or two or more members selected from a group consisting of a gellan gum, an agar, and a copolymer comprising 2-acrylamido-2-methylpropanesulfonic acid. Particularly preferably, the hydrophilic thickener comprises at least the gellan gum and comprises any one or both of agar and a copolymer comprising 2-acrylamido-2-methylpropanesulfonic acid in addition thereto.

In the present invention, the hydrophilic thickener (component (A)) is preferably contained in the form of a gel prepared in advance.

The method for preparing the gel is not particularly limited, and a general method can be used. Hereinafter, a typical preparation method will be described.

First, the hydrophilic thickener is dissolved in water arbitrarily containing an aqueous component. Then, the solution is left and cooled for solidification to form a gel. The dissolution of the thickener in water (or an aqueous component) can be performed by mixing, heating, or the like. The gelling (solidification) is performed by terminating heating after dissolving and standing the solution until the temperature becomes lower than the gelling temperature (solidification temperature).

The aqueous component is not particularly limited as long as the aqueous component can be used in the cosmetic and pharmaceutical fields. Examples thereof include glycols such as 1,3-butylene glycol and propylene glycol, lower alcohols (alcohols having less than 6 carbon atoms) such as ethanol and propanol, and components that are generally added as water phase components for cosmetics. Examples of the water phase component include, but are not limited to, chelating agents such as metaphosphate and edetate, pH adjusters, and preservatives. In the case of using the gellan gum as the hydrophilic thickener, a cation may be added into the aqueous component in order to further improve gel strength. Such a cation is not particularly limited and is preferably a monovalent or divalent cation. Specific examples thereof include acids that release a monovalent cation ($H^+$), for example, acetic acid and citric acid, and salts that are sources for a monovalent or divalent cation such as $Mg^{2+}$, $Ca^{2+}$, $Na^+$, and $K^+$, for example, magnesium chloride, calcium chloride, sodium chloride, and potassium chloride.

The hydrophilic thickener (A) according to the present invention may be contained in the form of a microgel preferably having an average particle size of 0.1 to 1000 µm, instead of the gel or in addition to the gel.

The microgel can be obtained by crushing the gel formed as described above with a homogenizer, a disper mixer (disper), a mechanical stirrer, or the like. The average particle size of the microgel that is suitably used in the present invention is usually 0.1 to 1,000 µm, preferably on the order of 1 to 300 µm, more preferably on the order of 10 to 200 µm.

The content of the hydrophilic thickener (component (A)) in the cosmetic of the present invention is not particularly limited and is preferably 0.3 to 5.0% by mass, more preferably 0.4 to 4.0% by mass, further preferably 0.5 to 3.0% by mass, with respect to the total amount of the cosmetic.

(B) Higher Alcohol

The higher alcohol (B) in the cosmetic of the present invention forms an associate (including an "α-gel") having a lamellar liquid crystal structure together with the surfactant (C) and the water (D) mentioned later. In the present specification, the higher alcohol (B) and the surfactant (C) are also referred to as "α-gel constituents".

The higher alcohol (B) (also referred to as a "component (B)") for use in the cosmetic of the present invention is not particularly limited as long as the alcohol has 6 or more carbon atoms and can be used in the cosmetic, pharmaceutical, and quasi drug fields, etc. The higher alcohol (B) includes a linear or branched saturated or unsaturated monohydric alcohol. Examples of the linear alcohol include saturated alcohols such as dodecanol (lauryl alcohol), tridodecanol, tetradodecanol (myristyl alcohol), pentadecanol, hexadecanol (cetyl alcohol), heptadecanol, octadecanol (stearyl alcohol), nonadecanol, icosanol (aralkyl alcohol), heneicosanol, docosanol (behenyl alcohol), tricosanol, tetracosanol (carnaubyl alcohol), pentacosanol, hexacosanol (seryl alcohol), oleyl alcohol, and cetostearyl alcohol, and unsaturated alcohols such as elaidyl alcohol. Examples of the branched alcohol include monostearyl glycerin ether (batyl alcohol), 2-decyltetradecinol, lanolin alcohol, cholesterol, phytosterol, hexyldodecanol, isostearyl alcohol, and octyldodecanol. These higher alcohols can be used in combination. In the present invention, a saturated linear monohydric alcohol is particularly preferred from the viewpoint of temporal stability.

A higher alcohol having a melting point of 60° C. or higher, for example, behenyl alcohol or stearyl alcohol, is preferably used as the higher alcohol (B). In the present invention, one or two or more of the higher alcohols described above can be used. In the case of using a mixture of two or more higher alcohols, a combination is preferably selected such that the melting point of the mixture is 60° C. or higher.

The content of the higher alcohol (B) is preferably 0.1 to 10% by mass, more preferably 0.1 to 7.0% by mass, further preferably 0.1 to 5% by mass, with respect to the total amount of the cosmetic. If the content of the higher alcohol (D) is less than 0.1% by mass or more than 10% by mass, sufficient emulsification stability may not be obtained.

(C) Surfactant

The surfactant (C) for use in the oil-in-water emulsion cosmetic of the present invention is at least one member selected from a group consisting of a nonionic surfactant and an ionic (anionic, cationic and amphoteric) surfactant. A hydrophilic surfactant having an HLB value of 10 or higher is preferably used as the nonionic surfactant.

The nonionic surfactant having an HLB value of 10 or higher for use in the present invention can be selected from a group consisting of, for example, polyethylene glycol fatty acid ester, polyoxyethylene fatty acid glyceryl, polyoxyethylene-methylpolysiloxane copolymers, fatty acid polyoxyethylene sorbitan, polyoxyethylene alkyl ether, maltitol hydroxy aliphatic alkyl ether, alkylated polysaccharides, alkylglucoside, sucrose fatty acid ester, polyoxyethylene hydrogenated castor oil glyceryl, polyoxyethylene sorbitol fatty acid ester, polyoxyethylene-polyoxypropylene block copolymers, tetrapolyoxyethylene-tetrapolyoxypropylene-ethylenediamine condensates, polyoxyethylene-beeswax-lanolin derivatives, alkanolamide, polyoxyethylene-propylene glycol fatty acid ester, polyoxyethylene-alkylamine, polyoxyethylene-fatty acid amide, alkylethoxydimethylamine oxide, and trioleyl phosphate.

Preferred examples of the nonionic surfactant having an HLB value of 10 or higher include, but are not limited to, polyethylene glycol monostearate (PEG-40 stearate, etc.), polyoxyethylene sorbitan monostearate (polysorbate 60, etc.), and polyoxyethylene behenyl ether (Beheneth-20). One or two or more of these nonionic surfactants can be used. The HLB value of two or more nonionic surfactants is calculated by weighted-averaging the respective HLB values of the surfactants according to the contents of the surfactants, and the value can be 10 or higher.

The ionic surfactant for use in the present invention includes an anionic surfactant, a cationic surfactant, and an amphoteric surfactant.

Examples of the anionic surfactant preferred for the present invention include, but are not particularly limited to, N-cocoyl glutamate, coconut oil fatty acid methyltaurine salt, N-caproyl methyltaurine salt, N-lauroyl methyltaurine salt, N-myristoyl methyltaurine salt, N-palmitoyl methyltaurine salt, N-stearoyl methyltaurine salt, N-oleoyl methyltaurine salt, N-cocoyl glutamate, N-lauroyl glutamate, N-myristoyl glutamate, N-palmitoyl glutamate, N-stearoyl glutamate, N-oleoyl glutamate, lauryl phosphate, myristyl phosphate, palmityl phosphate, and stearyl phosphate. Preferred examples of the counterion include sodium, potassium, triethanolamine, and ammonia.

Examples of the cationic surfactant preferred for the present invention include, but are not particularly limited to, lauryl trimethyl ammonium chloride, lauryl trimethyl ammonium bromide, myristyl trimethyl ammonium chloride, myristyl trimethyl ammonium bromide, cetyl trimethyl ammonium chloride, cetyl trimethyl ammonium bromide, stearyl trimethyl ammonium chloride, stearyl trimethyl ammonium bromide, behenyl trimethyl ammonium chloride, behenyl trimethyl ammonium bromide, cetyl trimethyl ammonium methanesulfonate, stearyl trimethyl ammonium methosulfate, myristyl dimethyl benzyl ammonium chloride, cetyl dimethyl benzyl ammonium chloride, stearyl dimethyl benzyl ammonium chloride, octyl dihydroxyethyl methyl ammonium chloride, 2-decyl tetradecyl trimethyl ammonium chloride, 2-dodecyl hexadecyl trimethyl ammonium chloride, stearoxypropyl trimethyl ammonium chloride, and N-(2-hydroxy-3-stearoxypropyl)-N,N-dimethylamine bromide.

Examples of the amphoteric surfactant preferred for the present invention include, but are not particularly limited to, imidazoline-based amphoteric surfactants such as sodium 2-undecyl-N,N,N-(hydroxyethylcarboxymethyl)-2-imidazoline, and 2-cocoyl-2-imidazolinium hydroxide-1-carboxyethyloxy disodium salt, betaine-based surfactants such as 2-heptadecyl-N-carboxymethyl-N-hydroxyethylimidazolinium betaine, lauryl dimethylaminoacetic acid betaine, alkyl betaine, amide betaine, and sulfobetaine, and cocamidopropyl betaine.

The cosmetic of the present invention can comprise at least one member selected from a nonionic surfactant and an ionic surfactant as the surfactant (C) and may contain two or more of the surfactants in combination. For example, a preferred embodiment of the cosmetic of the present invention contains at least one nonionic surfactant having an HLB value of 10 or higher and further contains at least one member selected from a group consisting of a nonionic surfactant and an ionic surfactant.

The content of the surfactant (C) is preferably 0.1 to 20% by mass, more preferably 0.2 to 10% by mass, further preferably 0.3 to 5% by mass, with respect to the total amount of the oil-in-water emulsion cosmetic. If the content of the surfactant (C) is less than 0.1% by mass or more than 20% by mass, sufficient emulsification stability may not be obtained.

A feature of the oil-in-water emulsion cosmetic of the present invention is an excellent "picking us" that is achieved by adjusting the mass ratio between the content of the hydrophilic thickener (A) and the total content of the higher alcohol (B) and the surfactant (C) (i.e., the "α-gel constituents") ([hydrophilic thickener]:[α-gel constituents]) to within the range of 3:1 to 1:9, preferably within the range of 2.5:1 to 1:8, more preferably within the range of 2:1 to 1:7. The mass ratio outside the range of 3:1 to 1:9 is not preferred because the cosmetic becomes a cream not a solid, or exhibits a poor picking up even in a solid state.

Further, the total content of the hydrophilic thickener and the α gel constituents is preferably within the range of 2.0 to 7.5% by mass, more preferably within the range of 2.5 to 7.0% by mass. When the total content is adjusted to within the range described above, not only picking up properties are excellent but particularly fresh texture of use can be conferred. If the total content is less than 2.0% by mass, the hardness of the cosmetic may be insufficient. If the total content is more than 7.5% by mass, freshness tends to lose.

(D) Water

The water (D) (also referred to as a "component (D)") for use in the cosmetic of the present invention is not particularly limited. Specific examples thereof include purified water and ion exchange water.

The content of the water (D) is preferably 25 to 90% by mass, more preferably 30 to 80% by mass, most preferably 35 to 70% by mass, with respect to the total amount of the oil-in-water emulsion cosmetic. If the content of the water (D) falls outside the range described above, the stability of the oil-in-water emulsion cosmetic may be worsened, or fresh usability may be harmed.

(E) Oil

The oil (E) (also referred to as a component (E)) for use in the oil-in-water emulsion cosmetic of the present invention constitutes the inner phase (oil phase) of the oil-in-water emulsion, together with the component (B) and the component (C). The oil that can be used in the present invention is not particularly limited and can be selected from hydrocarbon oil, ester oil, silicone oil, fat and oil, a fragrance, an oil-soluble ultraviolet absorber, and the like for use in cosmetic products.

Examples of the hydrocarbon oil include liquid paraffin, squalane, squalene, paraffin, isoparaffin, ceresin, isododecane, isohexadecane, ozokerite, pristane, and Vaseline.

Examples of the ester oil can include pentaerythrityl tetraethylhexanoate, cetyl ethylhexanoate, jojoba oil, di(phytosteryl/octyldodecyl) lauroyl glutamate, triisostearin, glyceryl diisostearate, triethylhexanoin, dimer dilinoleic acid (phytosteryl/behenyl), dimer dilinoleic acid (phytosteryl/isostearyl/cetyl/stearyl/isostearyl/cetyl/stearyl/behenyl), isopropyl palmitate, macadamia nut fatty acid phytosteryl, pentaerythrityl tetra(behenate/benzoate/ethylhexanoate), ethylhexyl palmitate, myristyl myristate, isopropyl myristate, tripropylene glycol dipivalate, diisopropyl sebacate, isodecyl neopentanoate, octyl octanoate, nonyl nonanoate, cetyl octanoate, octyldodecyl myristate, butyl stearate, hexyl laurate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, tripropylene glycol pivalate, diisostearyl malate, glycerin di-2-heptylundecanoate, glycerin diisostearate, trimethylolpropane tri-2-ethylhexanoate, trimethylolpropane triisostearate, pentaerythritol tetra-2-ethylhexanoate, glycerin tri-2-ethylhexanoate, glycerin trioctanoate, glycerin triisopalmitate, cetyl 2-ethylhexanoate-2-ethylhexyl palmitate, glycerin trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid-2-octyl dodecyl ester, di-2-heptylundecyl adipate, ethyl laurate, di-2-ethylhexyl sebacate, 2-hexyldecyl myristate, 2-hexyldecyl palmitate, 2-hexyldecyl adipate, 2-ethylhexyl succinate, and triethyl citrate.

Examples of the silicone oil include linear polysiloxane (e.g., dimethylpolysiloxane, methylphenylpolysiloxane, and diphenylpolysiloxane), cyclic polysiloxane (e.g., octamethylcyclotetrasiloxane, decamethylcyclopentasiloxane, and dodecamethylcyclohexasiloxane), silicone resin forming a three-dimensional network structure, a silicone rubber, a variety of modified polysiloxane (amino-modified polysiloxane, polyether-modified polysiloxane, alkyl-modified polysiloxane, fluorine-modified polysiloxane, etc.), and acrylic silicones.

Examples of the liquid fat and oil include flaxseed oil, camellia oil, macadamia nut oil, corn oil, mink oil, olive oil, avocado oil, *Camellia oleifera* seed oil, castor oil, safflower oil, rapeseed oil, soybean oil, peanut oil, triglycerin, turtle oil, egg yolk oil, sesame oil, persic oil, wheat germ oil, cottonseed oil, perilla oil, tea oil, *Torreya nucifera* seed oil, rice brain oil, *Paulownia fargesii* oil, *Paulownia tomentosa* oil, jojoba oil, and germ oil. Examples of the solid fat and oil include cacao butter, coconut oil, horse fat, hydrogenated coconut oil, palm oil, beef tallow, mutton tallow, hydrogenated beef tallow, palm kernel oil, lard, beef bone fat, Japan wax kernel oil, hydrogenated oil, neat's-foot oil, Japan wax, and hydrogenated castor oil.

Examples of the fragrance include, but are not particularly limited to, natural fragrances obtained from animals, or plants, synthetic fragrances produced by chemical synthesis approaches, and compounded fragrances which are mixtures thereof. When the fragrance is formulated in the cosmetic, such a cosmetic can be provided excellently with a long-term fragrance. Specific examples of the fragrance include Acetivenol®, anisaldehyde, anethole, amyl acetate, amyl salicylate, allyl amyl glycolate, allyl caproate, C6-C20 aldehydes, ambrettolide, ambrettolide, Ambroxan®, ionone, Iso E Super®, Eugenol®, Aurantiol®, Galaxolide®, calone, coumarin, geraniol, geranyl acetate, Sandalore®, santalol, Sandela®, cyclamen aldehyde, cis-3-hexenyl acetate, cis-3-hexenol, citral, citronellyl acetate, citronellol, cineole, dihydromyrcenol, jasmolactone, cinnamic alcohol, cinnamic aldehyde, styralyl acetate, cedryl acetate, cedrol, damascone, damascenone, decalactone, terpinyl acetate, terpineol, tonalid, Tonalide®, Triplal®, nerol, Bacdanol®, vanillin, hydroxycitronellal, phenylethyl acetate, phenylethyl alcohol, hexyl salicylate, vetiveryl acetate, Hedione®, heliotropin, helional, Vertofix®, benzyl acetate, benzyl salicylate, benzyl benzoate, Pentalide®, bornyl acetate, Mayol®, musk ketone, methyl anthranilate, methyl dihydrojasmonate, yara, lime oxide, linalyl acetate, linarol, limonene, Lyral®, Lilial®, rose oxide, rhodinol, Angelica oil, anise oil, *Artemisia vulgaris* oil, basil oil, bay oil, bergamot oil, calamus oil, camphor oil, *cananga* oil, cardamom oil, cassia oil, cedar wood oil, celery oil, chamomile oil, cinnamon oil, clove oil, coriander oil, cumin oil, dill oil, elemi oil, estragon oil, eucalyptus oil, fennel oil, fenugreek oil, galbanum oil, geranium oil, ginger oil, grapefruit oil, guaiac wood oil, cypress leaf oil, cypress oil, juniper berry oil, lavandin oil, lavender oil, lemon oil, lime oil, mandarin oil, ziram oil, mimosa oil, peppermint oil, spearmint oil, mill oil, myrtle oil, nutmeg oil, oakmoss oil, olibanum oil, opoponax oil, orange oil, parsley oil, patchouli oil, pepper oil, perilla oil, petit grain oil, neroli oil, orange flower oil, pimento oil, all spice oil, pine oil, rose oil, rosemary oil, clary sage oil, sage oil, sandalwood oil, styrax oil, taget oil, thyme oil, tuberose oil, valerian oil, vetiver oil, violet leaf oil, wintergreen oil, wormwood oil, ylang oil, yuzu oil, cassie absolute, genet absolute, hyacinth absolute, immortelle absolute, jasmine absolute, jonquil absolute, narcissus absolute, rose absolute, violet leaf absolute, and benzoin.

Examples of the oil-soluble ultraviolet absorber include: benzoic acid-based ultraviolet absorbers such as para-aminobenzoic acid (PABA), PABA monoglycerin ester, N,N-dipropoxy PABA ethyl ester, N,N-diethoxy PABA ethyl ester, N,N-dimethyl PABA ethyl ester, and N,N-dimethyl PABA butyl ester; anthranilic acid-based ultraviolet absorbers such as homomenthyl-N-acetyl anthranilate; salicylic acid-based ultraviolet absorbers such as amyl salicylate, menthyl salicylate, homomenthyl salicylate, octyl salicylate, phenyl salicylate, benzyl salicylate, and p-isopropanol phenyl salicylate; cinnamic acid-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate, 2-ethylhexyl-p-methoxycinnamate, 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate, glyceryl mono-2-ethylhexanoyl-di-para-methoxycinnamate, and 3-methyl-4-[methylbis(trimethylsiloxy)silyl]butyl 3,4,5-trimethoxycinnamate; and 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenylbenzotriazole, dibenzaladine, dianisoylmethane, 4-methoxy-4'-t-butyldibenzoylmethane, 5-(3,3-dimethyl-2-norbornylidene)-3-pentan-2-one, and octocrylene.

The content of the oil (component (E)) in the cosmetic of the present invention is not particularly limited and is preferably 5 to 30% by mass, more preferably 10 to 25% by mass, with respect to the total amount of the cosmetic.

The oil (component (E)) according to the present invention preferably contains an oil that is in a liquid state (liquid oil) at ordinary temperature (25° C.). A solid oil such as Japan wax may be added to the cosmetic, though the content thereof is within a range that does not inhibit the effect of the present invention. The content of the solid oil (wax, etc.) is, for example, less than 5.0% by mass, preferably 3.0% by mass or less, more preferably 1.0% by mass or less. The present invention encompasses an embodiment containing no wax.

The cosmetic of the present invention can contain other optional components that are usually added to cosmetics, etc., without impairing the effect of the present invention, in addition to the essential components (A) to (E) described above. Examples of other optional components include, but are not limited to, water-soluble ultraviolet absorbers, moisturizing agents, hydrophilic or lipophilic thickeners (except for the component (A)), powders, lower alcohols (having less than 6 carbon atoms), antioxidants, buffers, various drugs, stabilizers, preservatives, and dyes.

Examples of the water-soluble ultraviolet absorber include benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone, benzimidazole-based ultraviolet absorbers such as phenylbenzimidazole-5-sulfonic acid and salts thereof, and phenylene-bis-benzimidazole-tetrasulfonic acid and salts thereof, and 3-(4'-methylbenzylidene)-d,l-camphor, 3-benzylidene-d,l-camphor, urocanic acid, and urocanic acid ethyl ester.

The cosmetic of the present invention can contain a powder in the outer phase (water phase) and/or the inner phase (oil phase). Preferably, a hydrophilic powder is used when contained in the outer phase (water phase), and a powder having hydrophobic surface or a hydrophilic powder having hydrophobized surface (hydrophobic powder) is used when contained in the inner phase (oil phase), from the viewpoint of stability. The powder to be contained is not particularly limited by its shape or particle size.

Examples of the powder component that can be dispersed in the outer water phase include inorganic powders (e.g., talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, fired calcium sulfate (calcined gypsum), calcium phosphate, fluorapatite, hydroxyapatite, ceramic powder, metallic soap (e.g., zinc myristate, calcium palmitate, and aluminum stearate), and boron nitride), organic powders (e.g., polyamide resin powder (nylon powder), polyethylene powder, polymethyl methacrylate powder, polystyrene powder, powder of copolymer resin of styrene and acrylic acid, benzoguanamine resin powder, polytetrafluoroethylene powder, and cellulose powder), inorganic white pigments (e.g., titanium dioxide and zinc oxide), inorganic red pigments (e.g., iron oxide (colcothar) and iron titanate), inorganic brown pigments (e.g., γ-iron oxide), inorganic yellow pigments (e.g., yellow iron oxide and loess), inorganic black pigments (e.g., black iron oxide and titanium suboxide), inorganic purple pigments (e.g., mango violet and cobalt violet), inorganic green pigments (e.g., chromium oxide, chromium hydroxide, and cobalt titanate), inorganic blue pigments (e.g., ultramarine blue and iron blue), pearl pigments (e.g., titanium oxide coated mica, titanium oxide coated bismuth oxychloride, titanium oxide coated talc, coloration titanium oxide coated mica, bismuth oxychloride, and fish scale flakes), metal powder pigments (e.g., aluminum powder and copper powder), organic pigments such as zirconium, barium or aluminum rake (e.g., organic pigments such as red 201, red 202, red 204, red 205, red 220, red 226, red 228, red 405, orange 203, orange 204, yellow 205, yellow 401 and blue 404; and red 3, red 104, red 106, red 227, red 230, red 401, red 505, orange 205, yellow 4, yellow 5, yellow 202, yellow 203, green 3 and blue 1), and natural dyes (e.g., chlorophyll and β-carotene).

The powder component that can be dispersed in the inner oil phase is not particularly limited as long as the powder has hydrophobic surface. Examples thereof include powders themselves having hydrophobicity, such as silicone resin powder and fluorine resin powder as well as inorganic powders with their particle surface hydrophobized by a wet method (using a solvent), a vapor phase method, a mechanochemical method, or the like using silicones such as methyl hydrogen polysiloxane and dimethylpolysiloxane, dextrin fatty acid ester, higher fatty acid, higher alcohols, fatty acid ester, metallic soap, alkyl ether phosphate, fluorine compounds, or hydrocarbons such as squalane and paraffin. The average particle size of the hydrophobic powder needs to be smaller than that of the emulsion particles serving as the oil phase of the present invention. Particularly, in the case of using a powder as an ultraviolet scattering agent, its average particle size after crushing in a wet disperser is preferably 100 nm or smaller. Examples of the inorganic powder particles to be hydrophobized include titanium oxide, zinc oxide, talc, mica, sericite, kaolin, mica titanium, black iron oxide, yellow iron oxide, colcothar, ultramarine blue, iron blue, chromium oxide, and chromium hydroxide.

For adding the hydrophobic powder to the inner phase, it is preferred to add a dispersant. The dispersant used is not limited and is preferably a nonionic surfactant having HLB of 8 or higher and/or higher fatty acid.

Examples of the nonionic surfactant having HLB of 8 or higher include sorbitan sesquiisostearate, glyceryl stearate, and sorbitan triisostearate.

Examples of the higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), and docosahexaenoic acid (DHA). Isostearic acid is particularly preferred.

Examples of the antioxidant include tocopherols, dibutylhydroxytoluene, butylhydroxyanisole, and gallic acid ester. Examples of the antioxidation aid include phosphoric acid, citric acid, ascorbic acid, maleic acid, malonic acid, succinic acid, fumaric acid, cephalin, hexametaphosphate, phytic acid, and ethylenediaminetetraacetic acid.

Other examples of the component that may be optionally contained include preservatives (methylparaben, ethylparaben, butylparaben, phenoxyethanol, etc.), antiphlogistic agents (e.g., glycyrrhizic acid derivatives, glycyrrhetinic acid derivatives, salicylic acid derivatives, hinokitiol, zinc oxide, and allantoin), whitening agents (e.g., placenta extracts, *Saxifraga stolonifera* extracts, and arbutin), various extracts (e.g., *Phellodendri cortex*, goldthread, *Lithospermum* root, *Paeonia lactiflora, Swertia japonica*, birch, sage, loquat, carrot, aloe, *Malva mauritiana* L., iris, grape, *Coix ma-yuen*, sponge gourd, lily, saffron, *Cnidium officinale*, sheng jiang, *Hypericum erectum, Ononis*, garlic, chile pepper, chen pi, *Ligusticum acutilobum*, and seaweed), activators (e.g., royal jelly, photosensitive elements, and cholesterol derivatives), blood circulation promoting agents (e.g., nonanoic acid vanillylamide, nicotinic acid benzyl ester, nicotinic acid β-butoxy ethyl ester, capsaicin, gingeron, cantharis tincture, ichthammol, tannic acid, α-borneol, tocopherol nicotinate, inositol hexanicotinate, cyclandelate, cinnarizine, tolazoline, acetylcholine, verapamil, cepharanthine, and γ-oryzanol), anti-seborrhea agents (e.g., sulfur and thianthol), and anti-inflammatory agents (e.g., tranexamic acid, thiotaurine, and hypotaurine).

The oil-in-water emulsion solid cosmetic of the present invention can be produced, for example, but not limited to, by dissolving the oil (E), the higher alcohol (B), and the surfactant (C) at a high temperature to prepare a dissolved oil part, adding the dissolved oil part to a warmed water phase part containing the water (D) and other aqueous components, emulsifying the mixture by a routine method, and adding the hydrophilic thickener (A) to the emulsion.

The oil-in-water emulsion solid cosmetic of the present invention can be provided as a makeup cosmetic such as a foundation, a UV care cosmetic such as a sunscreen, or a skin care cosmetic by exploiting its features such as favorable picking up, fresh texture, and an excellent moisturizing effect.

EXAMPLES

Hereinafter, the present invention will be described further specifically with reference to Examples. However, the present invention is not limited by these examples. Contents represent % by mass with respect to the total amount unless otherwise specified.

Oil-in-water emulsion cosmetics were produced according to the formulations listed in Tables 1 to 4 described below, and evaluated for items given below. The results are also shown in Tables 1 to 4.

(1) Properties

A container of each produced cosmetic (sample) is tilted 45° under a condition of 25° C., and the presence or absence of flow of the cosmetic inside the container was visually confirmed 10 seconds later.

Solid: the cosmetic (sample) inside the container did not flow even when the container was tilted.

Cream: the cosmetic (sample) inside the container flowed when the container was tilted.

(2) Picking Up and (3) Freshness

As for (2) picking up and (3) freshness, each produced cosmetic (sample) was actually used by ten expert panelists and evaluated for "good picking up" and "freshness" on a 4-point scale.

A+: nine or more out of the ten panelists rated the sample as [excellent].

A: seven or more out of the ten panelists rated the sample as [excellent].

B: five or more out of the ten panelists rated the sample as [excellent].

C: only four or less out of the ten panelists rated the sample as [excellent].

TABLE 1

| | | Comparative Example 1 | Comparative Example 2 | Example 1 | Example 2 | Example 3 | Example 4 | Example 5 | Comparative Example 3 | Comparative Example 4 |
|---|---|---|---|---|---|---|---|---|---|---|
| Water | Ion exchange water | 56.5 | 57 | 57.5 | 58.25 | 58.5 | 59 | 59.5 | 59.75 | 60 |
| Moisturizing agent | 1,3-Butylene glycol | 5 | 5 | 5 | 5 | 5 | 5 | 5 | 5 | 5 |
| Preservative | Phenoxyethanol | 0.5 | 0.5 | 0.5 | 0.5 | 0.5 | 0.5 | 0.5 | 0.5 | 0.5 |
| Hydrophilic thickener | Gellan gum | 2.8 | 2.4 | 2 | 1.4 | 1.2 | 0.8 | 0.4 | 0.2 | 0 |
| | Cross-linked type (N,N-dimethylacrylamide-sodium 2-acrylamido-2-methylpropane-sulfonate) copolymer | 0.7 | 0.6 | 0.5 | 0.35 | 0.3 | 0.2 | 0.1 | 0.05 | 0 |
| Hydrophilic | Nonporous silica powder | 3 | 3 | 3 | 3 | 3 | 3 | 3 | 3 | 3 |
| α gel constituent | Polyethylene glycol monostearate | 0 | 0.1 | 0.2 | 0.35 | 0.4 | 0.5 | 0.6 | 0.65 | 0.7 |
| | Polyoxyethylene sorbitan monostearate | 0 | 0.1 | 0.2 | 0.35 | 0.4 | 0.5 | 0.6 | 0.65 | 0.7 |

TABLE 1-continued

|  |  | Comparative Example 1 | Comparative Example 2 | Example 1 | Example 2 | Example 3 | Example 4 | Example 5 | Comparative Example 3 | Comparative Example 4 |
|---|---|---|---|---|---|---|---|---|---|---|
| Oil | Behenyl alcohol | 0 | 0.3 | 0.6 | 1.05 | 1.2 | 1.5 | 1.8 | 1.95 | 2.1 |
|  | Isohexadecane | 5.5 | 5 | 4.5 | 3.75 | 3.5 | 3 | 2.5 | 2.25 | 2 |
|  | Isopropyl myristate | 5 | 5 | 5 | 5 | 5 | 5 | 5 | 5 | 5 |
|  | Trimethyl pentaphenyl trisiloxane | 5.55 | 5.55 | 5.55 | 5.55 | 5.55 | 5.55 | 5.55 | 5.55 | 5.55 |
|  | Octyl methoxycinnamate | 3 | 3 | 3 | 3 | 3 | 3 | 3 | 3 | 3 |
| Dispersant | Glyceryl stearate | 0.9 | 0.9 | 0.9 | 0.9 | 0.9 | 0.9 | 0.9 | 0.9 | 0.9 |
|  | Sorbitan triisostearate | 0.1 | 0.1 | 0.1 | 0.1 | 0.1 | 0.1 | 0.1 | 0.1 | 0.1 |
|  | Sorbitan sesquiisostearate | 1 | 1 | 1 | 1 | 1 | 1 | 1 | 1 | 1 |
|  | Isostearic acid | 1 | 1 | 1 | 1 | 1 | 1 | 1 | 1 | 1 |
| Hydrophobic powder | Silicone-treated pigmentary titanium oxide | 8 | 8 | 8 | 8 | 8 | 8 | 8 | 8 | 8 |
|  | Silicone-treated red iron oxide | 0.4 | 0.4 | 0.4 | 0.4 | 0.4 | 0.4 | 0.4 | 0.4 | 0.4 |
|  | Silicone-treated yellow iron oxide | 1.02 | 1.02 | 1.02 | 1.02 | 1.02 | 1.02 | 1.02 | 1.02 | 1.02 |
|  | Silicone-treated black iron oxide | 0.03 | 0.03 | 0.03 | 0.03 | 0.03 | 0.03 | 0.03 | 0.03 | 0.03 |
|  | Total | 100 | 100 | 100 | 100 | 100 | 100 | 100 | 100 | 100 |
| Hydrophilic thickener:α gel constituent (ratio) |  | 1:0 | 6:1 | 2.5:1 | 1:1 | 1:1.3 | 1:2.5 | 1:6 | 1:13 | 0:1 |
| Nature |  | Solid | Solid | Solid | Solid | Solid | Solid | Solid | Cream | Cream |
| Pick up |  | C | C | A | A+ | A+ | A+ | A+ | A+30 | A+ |

As shown in Table 1, the cosmetics of Examples 1 to 5 having a hydrophilic thickener:α-gel constituent ratio within the range of 3:1 to 1:9 were solid yet achieved favorable picking up. On the other hand, the cosmetic of Comparative Example 1 containing no α-gel constituent and the cosmetic of Comparative Example 2 having a ([hydrophilic thickener]:[α-gel constituent]) ratio outside the range due to the small proportion of the α gel constituents exhibited poor picking up. The cosmetic of Comparative Example 3 having a ([hydrophilic thickener]:[α-gel constituents]) ratio outside the range due to the small proportion of the hydrophilic thickener and the cosmetic of Comparative Example 4 containing no hydrophilic thickener did not become solid.

TABLE 2

|  |  | Example 6 | Example 7 | Example 4 | Example 8 | Example 9 | Example 10 | Example 11 |
|---|---|---|---|---|---|---|---|---|
| Water | Ion exchange water | 59.5 | 59.25 | 59 | 58.6 | 58 | 57.625 | 56.75 |
| Moisturizing agent | 1,3-Butylene glycol | 5 | 5 | 5 | 5 | 5 | 5 | 5 |
| Preservative | Phenoxyethanol | 0.5 | 0.5 | 0.5 | 0.5 | 0.5 | 0.5 | 0.5 |
| Hydrophilic thickener | Gellan gum | 0.4 | 0.6 | 0.8 | 1.2 | 1.6 | 1.8 | 2 |
|  | Cross-linked type (N,N-dimethylamylamide-sodium 2-amylamido-2-methylpropanesulfonate) copolymer | 0.1 | 0.15 | 0.2 | 0.3 | 0.4 | 0.45 | 0.5 |
| Hydrophilic powder | Nonporous silica | 3 | 3 | 3 | 3 | 3 | 3 | 3 |
| α gel constituent | Polyethylene glycol monostearate | 0.25 | 0.375 | 0.5 | 0.7 | 1 | 1.125 | 1.25 |
|  | Polyoxyethylene sorbitan monostearate | 0.25 | 0.375 | 0.5 | 0.7 | 1 | 1.125 | 1.25 |
|  | Behenyl alcohol | 0.75 | 1.125 | 1.5 | 2.25 | 3 | 3.375 | 3.75 |
| Oil | Isohexadecane | 4.25 | 3.625 | 3 | 1.75 | 0.5 | 0 | 0 |
|  | Isopropyl myristate | 5 | 5 | 5 | 5 | 5 | 5 | 5 |
|  | Trimethyl pentaphenyl trisiloxane | 5.55 | 5.55 | 5.55 | 5.55 | 5.55 | 5.55 | 5.55 |
|  | Octyl methoxycinnamate | 3 | 3 | 3 | 3 | 3 | 3 | 3 |
| Dispersant | Glyceryl stearate | 0.9 | 0.9 | 0.9 | 0.9 | 0.9 | 0.9 | 0.9 |
|  | Sorbitan triisostearate | 0.1 | 0.1 | 0.1 | 0.1 | 0.1 | 0.1 | 0.1 |
|  | Sorbitan sesquiisostearate | 1 | 1 | 1 | 1 | 1 | 1 | 1 |
|  | Isostearic acid | 1 | 1 | 1 | 1 | 1 | 1 | 1 |

TABLE 2-continued

|  |  | Example 6 | Example 7 | Example 4 | Example 8 | Example 9 | Example 10 | Example 11 |
|---|---|---|---|---|---|---|---|---|
| Hydrophobic powder | Silicone-treated pigmentary titaniumoxide | 8 | 8 | 8 | 8 | 8 | 8 | 8 |
|  | Silicone-treated red iron oxide | 0.4 | 0.4 | 0.4 | 0.4 | 0.4 | 0.4 | 0.4 |
|  | Silicone-treated yellow iron oxide | 1.02 | 1.02 | 1.02 | 1.02 | 1.02 | 1.02 | 1.02 |
|  | Silicone-treated black iron oxide | 0.03 | 0.03 | 0.03 | 0.03 | 0.03 | 0.03 | 0.03 |
|  | Total | 100 | 100 | 100 | 100 | 100 | 100 | 100 |
| Hydrophilic thickener:α gel constituent (ratio) |  | 1:2.5 | 1:2.5 | 1:2.5 | 1:2.4 | 1:2.5 | 1:2.5 | 1:2.5 |
| Hydrophilic thickener + α gel constituent (total) |  | 1.75 | 2.625 | 3.5 | 5.15 | 7.0 | 7.875 | 8.75 |
| Nature |  | Solid | Solid | Solid | Solid | Solid | Solid | Solid |
| Pick up |  | A+ | A+ | A+ | A+ | A+ | A+ | A+ |
| Freshness |  | A+ | A+ | A+ | A+ | A | B | C |

As shown in Table 2, the hydrophilic thickener:α-gel constituent ratio within the predetermined range was confirmed to achieve favorable picking up. However, when the total content of the hydrophilic thickener and the α-gel constituents fell short of 2% by mass, hardness was reduced (Example 6) though the cosmetic was solid (did not flow even when the container was tilted). On the other hand, the total content exceeding 7.5% by mass reduced freshness upon application though picking up was favorable (Examples 10 and 11).

TABLE 3

|  |  | Example 12 | Example 13 | Example 14 | Example 15 | Example 16 | Example 17 |
|---|---|---|---|---|---|---|---|
| Water | Ion exchange water | 59 | 59 | 59 | 59 | 59 | 59 |
| Moisturizing agent | 1,3-Butylene glycol | 5 | 5 | 5 | 5 | 5 | 5 |
| Preservative | Phenoxyethanol | 0.5 | 0.5 | 0.5 | 0.5 | 0.5 | 0.5 |
| Hydrophilic thickener | Gellan gum | 0.8 | 0.8 | 0.8 | 0.8 | 0.8 | 0 |
|  | Cross-linked type (N,N-dimethylaciylamide-sodium 2-acrylamido-2-methylpropanesulfonate) copolymer | 0.2 | 0.2 | 0 | 0.2 | 0.2 | 0.2 |
|  | Agar | 0 | 0 | 0.2 | 0 | 0 | 0.8 |
| Hydrophilic powder | Nonporous silica | 3 | 3 | 3 | 1 | 3 | 3 |
| α gel constituent | Polyethylene glycol monostearate | 0.5 | 0.5 | 0.5 | 0.5 | 0.5 | 0.5 |
|  | Polyoxyethylene sorbitan monostearate | 0.5 | 0.5 | 0.5 | 0.5 | 0.5 | 0.5 |
|  | Behenyl alcohol | 1.5 | 0 | 1.5 | 1.5 | 1.5 | 1.5 |
|  | Stearyl alcohol | 0 | 1.5 | 0 | 0 | 0 | 0 |
| Oil | Isohexadecane | 3 | 3 | 3 | 3 | 3 | 3 |
|  | Isopropyl myristate | 5 | 5 | 5 | 5 | 0 | 5 |
|  | Trimethyl pentaphenyl trisiloxane | 4 | 5.55 | 5.55 | 5.55 | 5.55 | 5.55 |
|  | Dimethicone | 0 | 0 | 0 | 0 | 5 | 0 |
|  | Octyl methoxycinnamate | 7 | 3 | 3 | 3 | 3 | 3 |
| Dispersant | Glyceryl stearate | 0.9 | 0.9 | 0.9 | 0.9 | 0.9 | 0.9 |
|  | Sorbitan triisostearate | 0.1 | 0.1 | 0.1 | 0.1 | 0.1 | 0.1 |
|  | Sorbitan sesquiisostearate | 1 | 1 | 1 | 1 | 1 | 1 |
|  | Isostearic acid | 1 | 1 | 1 | 1 | 1 | 1 |
| Hydrophobic powder | (Diphenyl dimethicone/vinyl diphenyl dimethicone/silsesquioxane) crosspolymer | 0 | 0 | 0 | 1 | 0 | 0 |
|  | (Vinyl dimethicone/methicone silsesquioxane) crosspolymer | 0 | 0 | 0 | 1 | 0 | 0 |
|  | Silicone-treated pigmentaiy titanium oxide | 0 | 8 | 8 | 8 | 8 | 8 |
|  | Silicone-treated fine particle titanium oxide | 3 | 0 | 0 | 0 | 0 | 0 |
|  | Silicone-treated fine particle zinc oxide | 4 | 0 | 0 | 0 | 0 | 0 |
|  | Silicone-treated red iron oxide | 0 | 0.4 | 0.4 | 0.4 | 0.4 | 0.4 |
|  | Silicone-treated yellow iron oxide | 0 | 1.02 | 1.02 | 1.02 | 1.02 | 1.02 |
|  | Silicone-treated black iron oxide | 0 | 0.03 | 0.03 | 0.03 | 0.03 | 0.03 |
|  | Total | 100 | 100 | 100 | 100 | 100 | 100 |

TABLE 3-continued

|  | Example 12 | Example 13 | Example 14 | Example 15 | Example 16 | Example 17 |
|---|---|---|---|---|---|---|
| Hydrophilic thickener:α gel constituent (ratio) | 1:2.5 | 1:2.5 | 1:2.5 | 1:2.5 | 1:2.5 | 1:2.5 |
| Hydrophilic thickener + α gel constituent (total) | 3.5 | 3.5 | 3.5 | 3.5 | 3.5 | 3.5 |
| Nature | Solid | Solid | Solid | Solid | Solid | Solid |
| Pick up | A+ | A+ | A+ | A+ | A+ | A+ |
| Freshness | A+ | A+ | A+ | A+ | A+ | A+ |

As shown in Table 3, provided that the hydrophilic thickener:α-gel constituent ratio is within the predetermined range of the present invention and the total content of the hydrophilic thickener and the α-gel constituents is within the range of 2.0 to 7.5% by mass, the resulting solid cosmetic exerts favorable picking up and freshness even if the type of the hydrophilic thickener or the higher alcohol is changed (Examples 13 and 14). Furthermore, favorable results were similarly obtained both when the powder to be contained was fine particle titanium dioxide and fine particle zinc oxide (Example 12) or a silicone resin powder (Example 15) and when the oil was supplemented with silicone oil (Example 16). Although the cosmetic of Example 17 containing no gellan gum in the hydrophilic thickener produced similar results, its hardness was slightly reduced so that the cosmetic was soft to a certain degree.

TABLE 4

|  |  | Example 18 | Example 19 | Example 20 | Example 21 | Example 22 | Example 23 |
|---|---|---|---|---|---|---|---|
| Water | Ion exchange water | 57.02 | 57.02 | 57.02 | 57.02 | 57.02 | 57.02 |
| Moisturizing agent | 1,3-Butylene glycol | 5 | 5 | 5 | 5 | 5 | 5 |
| Preservative | Phenoxyethanol | 0.5 | 0.5 | 0.5 | 0.5 | 0.5 | 0.5 |
| Hydrophilic thickener | Gellan gum | 0.8 | 0.8 | 0.8 | 0.8 | 0.8 | 0.8 |
|  | Cross-linked type (N,N-dimethylamylamide-sodium 2-amylamido-2-methylpropanesulfonate) copolymer | 0.2 | 0.2 | 0.2 | 0.2 | 0.2 | 0.2 |
| Hydrophilic powder | Nonporous silica | 3 | 3 | 3 | 3 | 3 | 3 |
| α gel constituent | Monosodium N-stearoyl-L-glutamate | 0.5 | 0 | 0 | 0 | 0 | 0 |
|  | Potassium N-cocoyl glutamate | 0 | 0.5 | 0 | 0 | 0 | 0 |
|  | Sodium N-stearoyl-N-methyltaurine | 0 | 0 | 0.5 | 0 | 0 | 0 |
|  | Stearyl trimethyl ammonium chloride | 0 | 0 | 0 | 0.5 | 0 | 0 |
|  | Behenyl trimethyl ammonium chloride | 0 | 0 | 0 | 0 | 0.5 | 0 |
|  | Cocamidopropyl betaine | 0 | 0 | 0 | 0 | 0 | 0.5 |
|  | Polyoxyethylene sorbitan monostearate | 0.5 | 0.5 | 0.5 | 0.5 | 0.5 | 0.5 |
|  | Behenyl alcohol | 1 | 1 | 1 | 1 | 0.5 | 1 |
|  | Stearyl alcohol | 0.5 | 0.5 | 0.5 | 0.5 | 1 | 0.5 |
| Oil | Isohexadecane | 3 | 3 | 3 | 3 | 3 | 3 |
|  | Isopropyl myristate | 5 | 5 | 5 | 5 | 5 | 5 |
|  | Trimethyl pentaphenyl trisiloxane | 5.55 | 5.55 | 5.55 | 5.55 | 5.55 | 5.55 |
|  | Dimethicone | 0 | 0 | 0 | 0 | 0 | 0 |
|  | Octyl methoxycinnamate | 3 | 3 | 3 | 3 | 3 | 3 |
| Dispersant | Glyceryl stearate | 0.9 | 0.9 | 0.9 | 0.9 | 0.9 | 0.9 |
|  | Sorbitan triisostearate | 0.1 | 0.1 | 0.1 | 0.1 | 0.1 | 0.1 |
|  | Sorbitan sesquiisostearate | 1 | 1 | 1 | 1 | 1 | 1 |
|  | Isostearic acid | 1 | 1 | 1 | 1 | 1 | 1 |
| Hydrophobic powder | (Diphenyl dimethicone/vinyl diphenyl dimethicone/silsesquioxane) crosspolymer | 0.5 | 0.5 | 0.5 | 0.5 | 0.5 | 0.5 |
|  | (Vinyl dimethicone/methicone silsesquioxane) crosspolymer | 0.5 | 0.5 | 0.5 | 0.5 | 0.5 | 0.5 |
|  | Silicone-treated pigmentaly titanium oxide | 7 | 7 | 7 | 7 | 7 | 7 |
|  | Silicone-treated fine particle titanium oxide | 1 | 1 | 1 | 1 | 1 | 1 |
|  | Silicone-treated fine particle zinc oxide | 1 | 1 | 1 | 1 | 1 | 1 |

TABLE 4-continued

|  | Example 18 | Example 19 | Example 20 | Example 21 | Example 22 | Example 23 |
|---|---|---|---|---|---|---|
| Silicone-treated red iron oxide | 0.4 | 0.4 | 0.4 | 0.4 | 0.4 | 0.4 |
| Silicone-treated yellow iron oxide | 1 | 1 | 1 | 1 | 1 | 1 |
| Silicone-treated black iron oxide | 0.03 | 0.03 | 0.03 | 0.03 | 0.03 | 0.03 |
| Total | 100 | 100 | 100 | 100 | 100 | 100 |
| Hydrophilic thickener:α-gel constituent (ratio) | 1:2.5 | 1:2.5 | 1:2.5 | 1:2.5 | 1:2.5 | 1:2.5 |
| Hydrophilic thickener + α-gel constituent (total) | 3.5 | 3.5 | 3.5 | 3.5 | 3.5 | 3.5 |
| Nature | Solid | Solid | Solid | Solid | Solid | Solid |
| Pick up | A+ | A+ | A+ | A+ | A+ | A+ |
| Freshness | A+ | A+ | A+ | A+ | A+ | A |

As shown in Table 4, the solid cosmetics containing the anionic surfactant as the surfactant (C) (Examples 18 to 20), the solid cosmetics containing the cationic surfactant (Examples 21 and 22) and the solid cosmetic containing the amphoteric surfactant (Example 23) exerted favorable picking up and freshness when satisfying the requirements of the present invention.

Other formulation examples of the cosmetic of the present invention will be described below. All the formulations were solid and were excellent in picking up and freshness.

(Formulation Example 1) Foundation

| 1,3-Propanediol | 8% |
|---|---|
| Phenoxyethanol | 0.5% |
| Gellan gum | 1% |
| Polyethylene glycol monostearate | 0.5% |
| Polyoxyethylene sorbitan monostearate | 0.5% |
| Stearyl alcohol | 1.5% |
| Isododecane | 3% |
| Triethylhexanoin | 5% |
| Trimethyl pentaphenyl trisiloxane | 5% |
| Octyl methoxycinnamate | 2% |
| Octocrylene | 1% |
| Glyceryl stearate | 1% |
| Sorbitan sesquiisostearate | 1% |
| Isostearic acid | 1% |
| Silicone-treated pigmentary titanium oxide | 7% |
| Silicone-treated red iron oxide | 0.3% |
| Silicone-treated yellow iron oxide | 1.2% |
| Silicone-treated black iron oxide | 0.02% |
| Ion exchange water | balance |

(Formulation Example 2) Sunscreen (1)

| 1,3-Propanediol | 8% |
|---|---|
| Phenoxyethanol | 0.5% |
| Gellan gum | 1% |
| Polyethylene glycol monostearate | 0.5% |
| Polyoxyethylene sorbitan monostearate | 0.5% |
| Stearyl alcohol | 1.5% |
| Isododecane | 3% |
| Octyl methoxycinnamate | 7% |
| Ethylhexyl triazone | 1% |
| 2-Hydroxy-4-methoxybenzophenone | 1% |
| Bis-ethylhexyloxyphenol methoxyphenyl triazine | 1% |
| Hexyl diethylaminohydroxybenzoylbenzoate | 2% |
| Glyceryl stearate | 1% |
| Sorbitan sesquiisostearate | 1% |
| Isostearic acid | 1% |
| Silicone-treated fine particle titanium oxide | 3% |

-continued

| Silicone-treated fine particle zinc oxide | 3% |
|---|---|
| Ion exchange water | balance |

(Formulation Example 3) Sunscreen (2)

| DPG | 8% |
|---|---|
| Methylparaben | 0.15% |
| Ethylparaben | 0.1% |
| Gellan gum | 1% |
| Polyethylene glycol monostearate | 0.5% |
| Polyoxyethylene sorbitan monostearate | 0.5% |
| Stearyl alcohol | 1.5% |
| Dimethicone | 3% |
| Octyl methoxycinnamate | 3% |
| Triethanolamine | 0.5% |
| Phenylbenzimidazole sulfonic acid | 1% |
| Glyceryl stearate | 1% |
| Sorbitan sesquiisostearate | 1% |
| Isostearic acid | 1% |
| Silicone-treated fine particle titanium oxide | 3% |
| Silicone-treated fine particle zinc oxide | 3% |
| Ion exchange water | balance |

(Formulation Example 4) Skin Care Cosmetic

| 1,3-Butylene glycol | 7% |
|---|---|
| Methylparaben | 0.15% |
| Ethylparaben | 0.1% |
| Gellan gum | 1% |
| Polyethylene glycol monostearate | 0.5% |
| Polyoxyethylene sorbitan monostearate | 0.5% |
| Stearyl alcohol | 1.5% |
| Dimethicone | 5% |
| Triethylhexanoin | 3% |
| Glyceryl stearate | 1% |
| Sorbitan sesquiisostearate | 1% |
| Isostearic acid | 1% |
| Ion exchange water | balance |

The invention claimed is:

1. An oil-in-water emulsion solid cosmetic, comprising:
(A) at least one hydrophilic thickener selected from the group consisting of a gellan gum, an agar and a copolymer of 2-acrylamido-2-methylpropanesulfonic acid;

(B) 0.75% to 3.75% higher alcohol;
(C) a surfactant;
(D) water; and
(E) an oil;
wherein a ratio between the content of said hydrophilic thickener (A) and the total content of said higher alcohol (B) and said surfactant (C) is within a range of 1:2.5 to 1:9.

2. The cosmetic, according to claim 1, wherein:
a total content of said hydrophilic thickener (A), said higher alcohol (B) and said surfactant (C) is within the range of 2.0 to 7.5% by mass.

3. The cosmetic, according to claim 1, wherein:
said hydrophilic thickener (A) comprises a gellan gum.

4. The cosmetic, according to claim 1, wherein:
said copolymer of 2-acrylamido-2-methylpropanesulfonic acid is a copolymer that is a cross-linked N,N-dimethylacrylamide-2-acrylamido-2-methylpropanesulfonic acid salt copolymer.

5. The cosmetic, according to claim 1, wherein:
said surfactant (C) comprises at least one member selected from the group consisting of a nonionic surfactant, an anionic surfactant, a cationic surfactant and an amphoteric surfactant.

6. The cosmetic, according to claim 1, wherein:
said surfactant (C) comprises a nonionic surfactant having an HLB value of at least 10.

7. The cosmetic, according to claim 1, further comprising:
a hydrophobic powder dispersed in an inner oil phase thereof.

8. The cosmetic, according to claim 1, further comprising:
a hydrophilic powder dispersed in an outer water phase thereof.

9. The cosmetic, according to claim 1, wherein:
said cosmetic is a skin care cosmetic, a sunscreen or a makeup cosmetic.

* * * * *